(12) United States Patent
DiCarlo et al.

(10) Patent No.: US 8,149,405 B2
(45) Date of Patent: Apr. 3, 2012

(54) COLOR ANALYSIS SYSTEM AND METHOD

(75) Inventors: Jeffrey M. DiCarlo, Menlo Park, CA (US); Melanie M. Gottwals, San Jose, CA (US); Steven W. Trovinger, Los Altos, CA (US); Glen E. Montgomery, San Jose, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 437 days.

(21) Appl. No.: 12/436,240

(22) Filed: May 6, 2009

(65) Prior Publication Data

US 2010/0284009 A1    Nov. 11, 2010

(51) Int. Cl.
*G01J 3/46* (2006.01)

(52) U.S. Cl. ........................................... 356/402

(58) Field of Classification Search .................. 356/402, 356/422; 347/19
See application file for complete search history.

(56) References Cited

U.S. PATENT DOCUMENTS

| | | | | |
|---|---|---|---|---|
| 4,699,510 A | * | 10/1987 | Alguard | 356/73 |
| 4,917,495 A | | 4/1990 | Steenhoek | |
| 5,150,174 A | * | 9/1992 | Ryczek et al. | 356/402 |
| 5,229,841 A | * | 7/1993 | Taranowski et al. | 356/406 |
| 5,642,189 A | * | 6/1997 | Alguard | 356/72 |
| 5,844,680 A | | 12/1998 | Sperling | |
| 6,057,912 A | * | 5/2000 | Celentano et al. | 356/326 |
| 6,351,308 B1 | * | 2/2002 | Mestha | 356/402 |
| 6,567,159 B1 | * | 5/2003 | Corech | 356/71 |
| 7,394,541 B1 | | 7/2008 | DiCarlo et al. | |
| 7,466,416 B2 | | 12/2008 | Baker et al. | |
| 2003/0169421 A1 | * | 9/2003 | Ehbets | 356/406 |
| 2007/0046941 A1 | | 3/2007 | Mestha et al. | |
| 2008/0174788 A1 | | 7/2008 | Ehbets et al. | |

FOREIGN PATENT DOCUMENTS

| | | |
|---|---|---|
| JP | 05-113370 A | 5/1993 |
| JP | 2001-050817 A | 2/2001 |
| JP | 2007-057529 A | 3/2007 |

* cited by examiner

*Primary Examiner* — Kara E Geisel

(57) ABSTRACT

A color analysis system includes a plurality of light sources configured to illuminate a test patch. A sensor is configured to receive light from the plurality of light sources reflected from the test patch. A controller is configured to determine the color of the test patch in response to light received by the sensor reflected from the first light source, and adjust the color determination in response to light received by the sensor reflected from the first and second light sources.

18 Claims, 4 Drawing Sheets

COLOR ANALYSIS SYSTEM AND METHOD

BACKGROUND

The colors produced by color printers can vary as a function of media type, ink, print heads, temperature, humidity, etc. Color management products allow the creation of device characterization profiles for devices such as printers. These profiles, such as International Color Consortium (ICC) compliant profiles, allow for proper color handling across many types of devices. For example, in order to create a printer profile, the printer outputs a test sheet of color patches arranged in a predetermined pattern. A color measurement device such as a spectrophotometer or calorimeter then scans the color patches, and the color measurements can be used create a profile for the printer that can be used to insure uniform color display.

However, known color measurement tools can be difficult to operate correctly, time consuming and expensive. For example, many hand held spectrophotometers include a contact device such as a wheel that contacts the color patches on the paper. This maintains a desired spatial relationship between the spectrophotometer and the paper, and as the spectrophotometer is moved, the wheel measures the speed and direction of the movement. Because the spectrophotometer device contacts the paper, it can distort the color patches, making the measurement by the spectrophotometer inaccurate.

In other known systems, a color measurement device such as a spectrophotometer or calorimeter is mounted in the paper path of the moving sheets in a printer to provide color measurements of the test color patches printed on the sheets as they pass the color measurement device. With a system such as this, the color measurement device does not contact the paper. However, such non-contact color measurement systems can be sensitive to variation in the distance between the color measurement device and the test color patches. Factors such as differences in media thickness or variations in a paper's position as it travels through a printer thus can reduce accuracy of the color measurement.

For these and other reasons, a need exists for the present invention.

DETAILED DESCRIPTION

In the following detailed description, reference is made to the accompanying drawings which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

In the following disclosure, specific details may be set forth in order to provide a thorough understanding of the disclosed systems and methods. It should be understood however, that all of these specific details may not be required in every implementation. In other instances, well-known methods, procedures, components, circuits, and networks have not been described in detail so as not to unnecessarily obscure the disclosed systems and methods.

It will also be understood that, although the terms first, second, etc. are used herein to describe various elements, these elements should not be limited by these terms. These terms are only used to distinguish one element from another.

Figure 1:
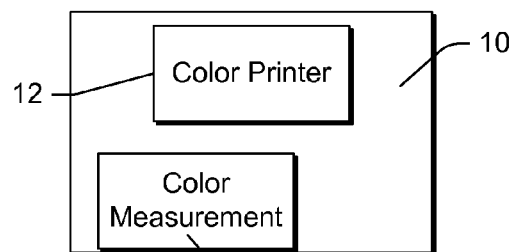
FIG. 1 is a block diagram conceptually illustrating an embodiment of a printer system.

FIG. 1 conceptually illustrates portions of an embodiment of a printer system 10, which includes a color printer 12, such as a color laser or ink printer. It is desirable for a color printer system to measure the colors of test patches on a printed test sheet. This allows for real-time, automatic printer color correction. Thus the printer system 10 includes a color analysis system 100. In the illustrated embodiments, the color analysis system 100 is configured as a non-contact system. In other words, the system 100 does not contact printed sheets produced by the printer 12.

Figure 2:
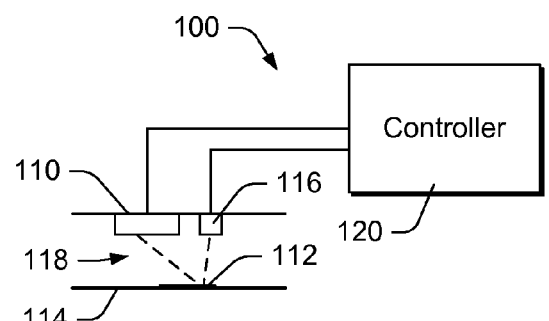
FIG. 2 is a block diagram conceptually illustrating an embodiment of a color analysis system.

FIG. 2 broadly illustrates aspects of an embodiment of the color analysis system 100. The system 100 includes a plurality of light sources 110 that are configured to illuminate a test patch 112 on a test sheet 114. A sensor 116 is configured to receive light 118 from the plurality of light sources 110 reflected from the test patch 112. A controller 120 receives an output signal from the sensor 116 and is configured to determine a color adjustment in response to the output of the sensor 116. Further, the controller 120 determines the color of the test patch 112 in response to the first sensor 116, and applies the color adjustment to the determined color.

Embodiments of the controller 120 may be implemented by one or more discrete modules (or data processing components) that are not limited to any particular hardware, firmware, or software configuration. In some embodiments, the controller 120 is a component of the printer 10, and in other embodiments, the color analysis system itself includes a dedicated controller 120. The controller 120 may be implemented in any computing or data processing environment, including in digital electronic circuitry (e.g., an application-specific integrated circuit, such as a digital signal processor (DSP)) or in computer hardware, firmware, device driver, or software. In some embodiments, the functionalities of the modules are combined into a single data processing component. In some embodiments, the respective functionalities of each of one or more of the modules are performed by a respective set of multiple data processing components.

In some implementations, process instructions (e.g., machine-readable code, such as computer software) for implementing the methods that are executed by the embodiments of the controller 120, as well as the data it generates, are stored in one or more machine-readable media. Storage devices suitable for tangibly embodying these instructions and data include all forms of computer-readable memory, including, for example, semiconductor memory devices, such as EPROM, EEPROM, and flash memory devices, magnetic disks such as internal hard disks and removable hard disks, magneto-optical disks, DVD-ROM/RAM, and CD-ROM/RAM.

Figure 3:
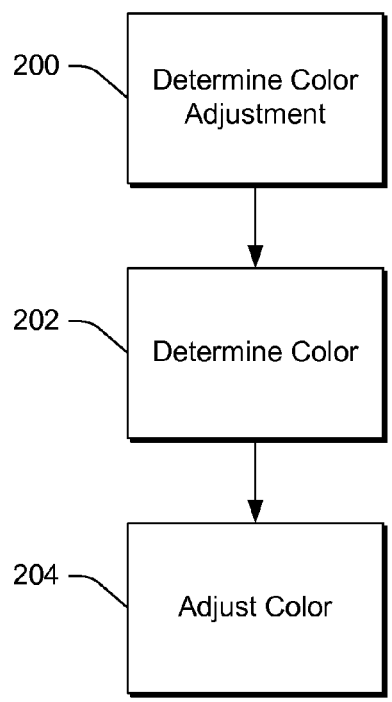
FIG. 3 is a flow diagram illustrating an embodiment of a color analysis method.

FIG. 3 broadly illustrates a color analysis method implemented by the color analysis system 100. In block 200, the system determines a color adjustment that varies with the height, or distance between the light sources 110 and the test patch 112. In block 202, the color of the test patch 112 is determined, then the color is adjusted in block 204.

Figure 5:
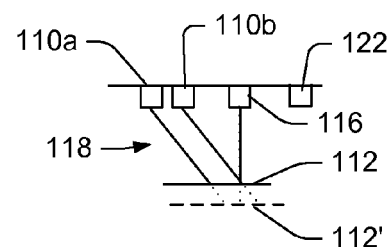
FIG. 5 is a block diagram conceptually illustrating aspects of an embodiment of a color analysis system.
Figure 4:
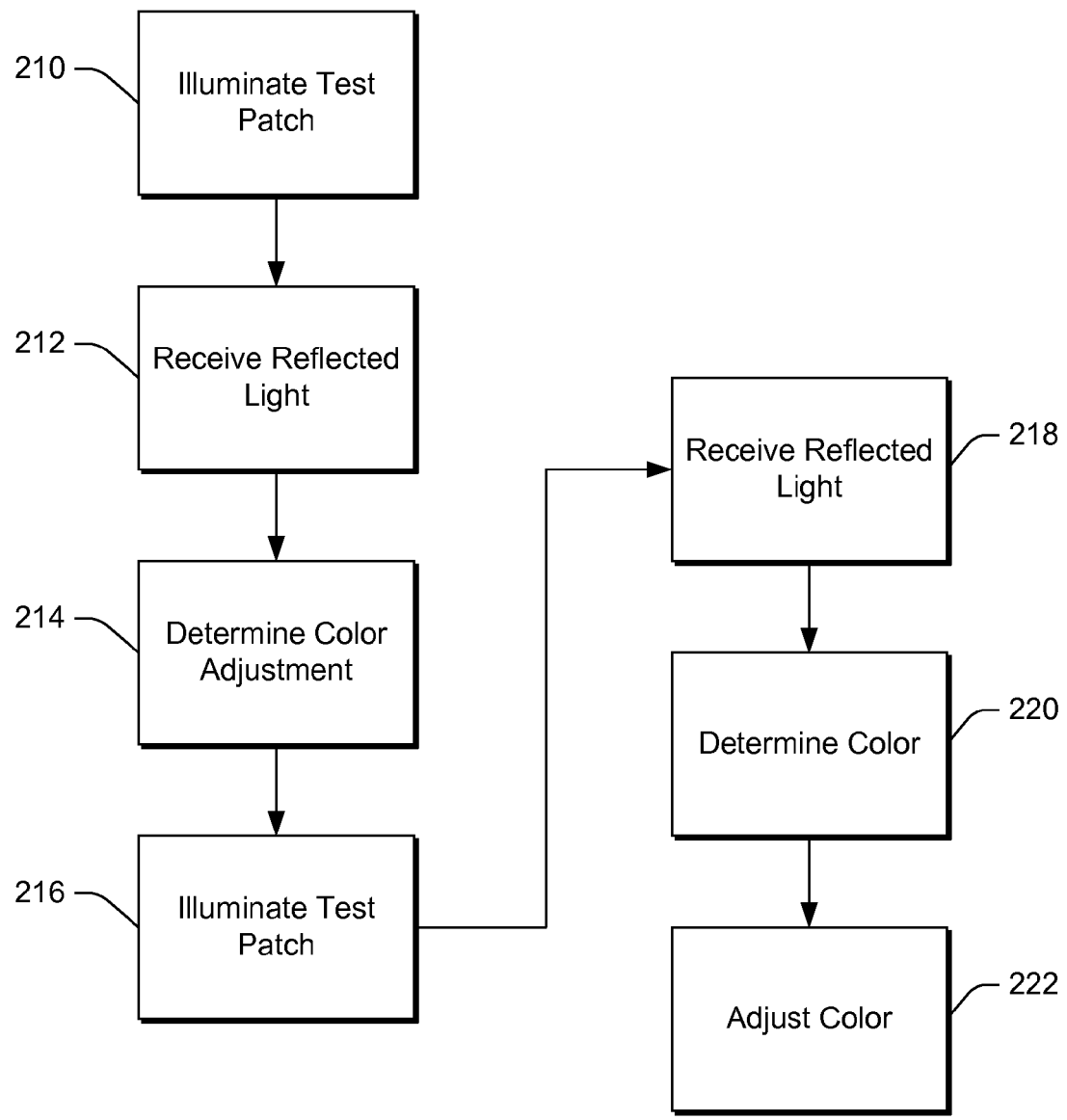
FIG. 4 is a flow diagram illustrating further aspects of the embodiment of the color analysis method illustrated in FIG. 3.

FIG. 4 illustrates further aspects of the color analysis process. The light sources 110 are used to illuminate the test patch 112 in block 210. In some embodiments, the light sources 110 are LEDs and the sensor 116 is a photo sensor that receives light reflected from the test patch 112 and outputs a diffuse signal. Two of the LEDs are used to determine the color adjustment. These two LEDs emit light having the same color, which in certain embodiments is red light having a nominal peak wavelength of 650 nm. As illustrated in FIG. 5, the two LEDs 110a and 110b are spaced apart from each other, and this spacing causes the light to reflect off of the test patch 112 at slightly different angles. As the distance between the LEDs 110a, 110b and the test patch 112 varies, for example, between the test patches 112 and 112', these angle differences causes the light pattern from each LED 110a, 110b to shift differently. The reflected light is received by the sensor 116 in Block 212 of FIG. 4, and by measuring the intensity of the reflected light from each LED 110a, 110b sequentially using the sensor 116 and taking the ratio of the result, a color adjustment can be determined as illustrated in Block 214.

Figure 6A:
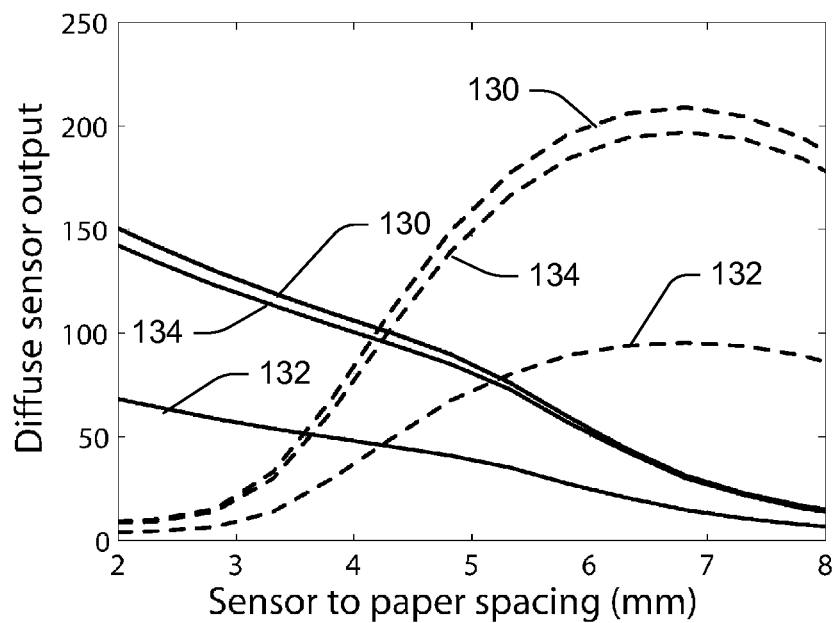
FIG. 6A illustrates intensity measurements as a function of height for different colored test patches.
Figure 6B:
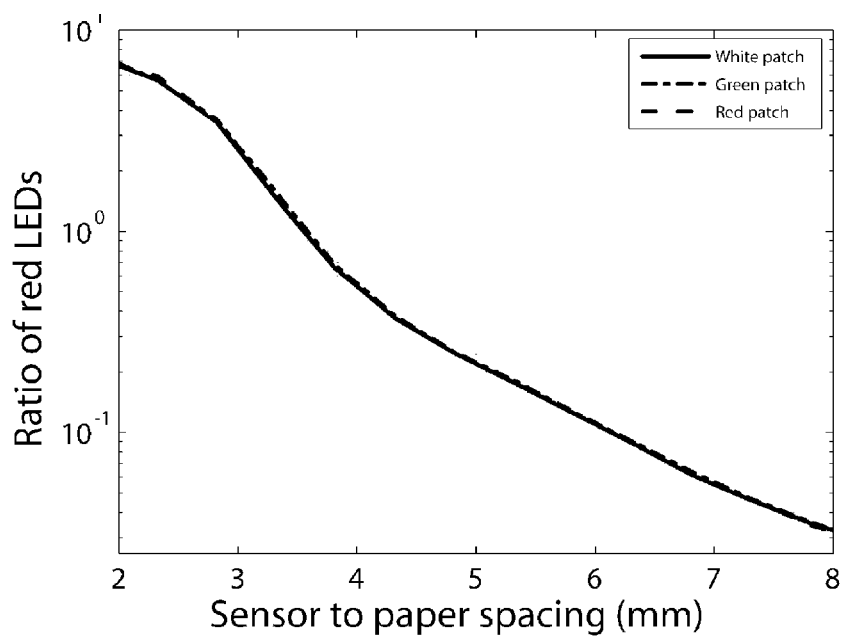
FIG. 6B illustrates ratios of the measurements illustrated in FIG. 6A.

FIG. 6A illustrates intensity measurements from two red LEDs as a function of height for different colored test patches, including white 130, green 132 and red 134 test patches. In FIG. 6A, the solid lines represent the sensor output for the first LED 110a and the broken lines represent the sensor output for the second LED 110b for each of the different colored test patches 130, 132 and 134. FIG. 6B illustrates the resulting ratios of the two measurements for the same test patches. The ratio plot of FIG. 6B shows a direct correlation between the ratio of the output signals of the sensor 116 for the two light sources and the module height. Moreover, because the LEDs are the same color, this ratio does not change for different colored patches or media types (assuming enough light is reflected from the patch). Thus, in accordance with certain embodiments, the color adjustment determined in block 214 is based on the ratio of reflected light received from the first LED to reflected light received from the second LED.

Some embodiments include a second photo sensor 122 that directly receives light from the light sources and measures changes in the LED intensities. This allows adjusting the system in response to any LED intensity shift over time.

Figure 7:
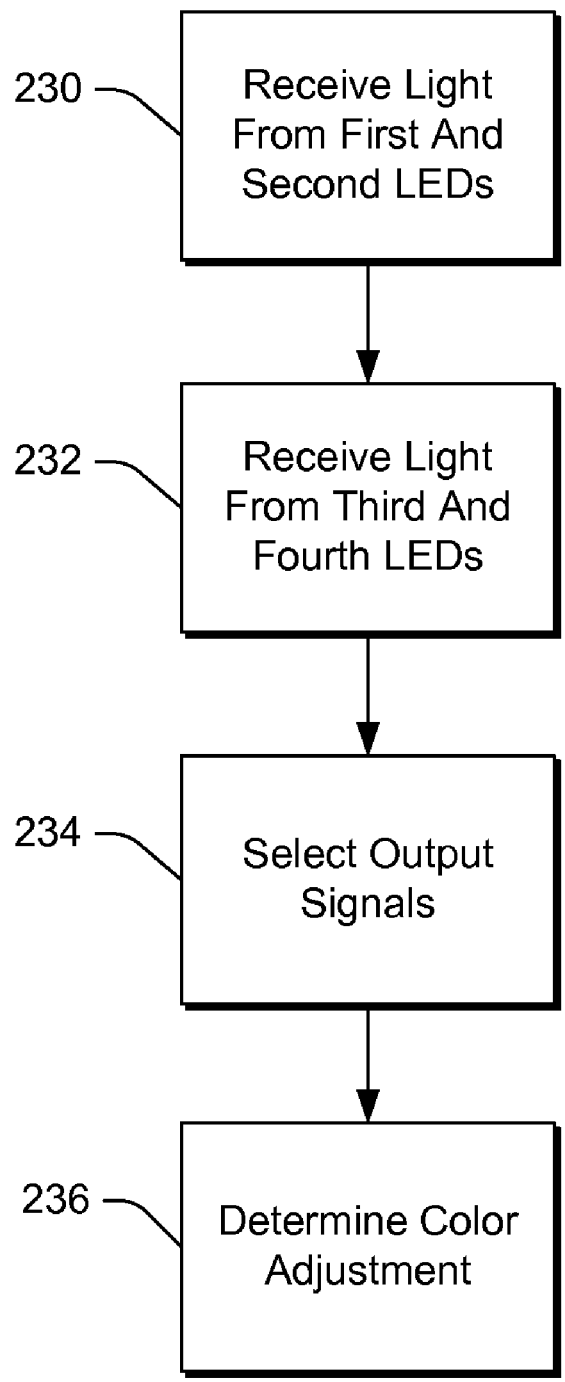
FIG. 7 is a flow diagram illustrating portions of an embodiment of a color analysis method.

In some embodiments, a second set of light sources are provided for use in determining the color adjustment, including third and fourth LEDs. The first and second LEDs emit light of a first color, and the second and third LEDs emit light of a second color. In an exemplary embodiment, the first and second LEDs emit red light, and the third and fourth LEDs emit cyan light. Both sets of LEDs are used to illuminate the test patch, and the output signals from one of the sets of LEDs is used to determine the color adjustment. FIG. 7 illustrates a method in accordance with such an embodiment.

In block 230 of FIG. 7, light reflected by the test patch 112 from the first and second LEDs is received by the sensor 116, and in block 232 light reflected by the test patch 112 from the third and fourth LEDs is received by the sensor 116. The sensor 116 outputs corresponding output signals to the controller 120 in response to the received light. In block 234, the output signals corresponding to either the first and second LEDs or the third and fourth LEDs are selected based on some predetermined criterion. For example, the light reflected from the test patch 112 will vary based on the color of the test patch. Thus, depending on the color of the test patch 112, the sensor 116 could receive more reflected light from the red LEDs than from the cyan LEDs or vice versa. Accordingly, the LEDs that provide a stronger signal are selected for use in determining the color adjustment, which includes determining the ratio of the reflected light received from the selected light sources.

The color analysis system 100 operates as a colorimeter. More specifically, it can reproduce color measurements (XYZ values, LAB values or spectral reflectance functions) that are valid for a set of predefined illuminants and any ink/media combination. (Measurements from a spectrophotometer are valid for any arbitrary illuminant.) In the illustrated embodiment, the light source 110 includes five LEDs in addition to the red (650 nm) LEDs used for the distance determination. One of the LEDs 110a, 110b is used for both the color adjustment determination and color measurement, so six LEDs in total are used for the color determination. In other embodiments, there are a total of eight LEDs, where two red LEDs and two cyan LEDs are used for the color adjustment determination, and one of the red and one of the cyan LEDs are used with the remaining four LEDs for the color determination.

The LEDs used for the color determination emit light at different peak wavelengths across the visible spectrum. In some embodiments, LEDs emitting light having nominal peak wavelengths of 450 nm, 470 nm, 520 nm, 560 nm, 610 nm and 650 nm are used for color sensing.

Referring back to FIG. 4, in block 216, the test patch 112 is illuminated in sequence using each of the six LEDs. The reflected light is received by the sensor 116 (and directly by the calibration sensor 122 where applicable) in block 218 and the output signal from the sensors 116, 122 is recorded. More particularly, in some implementations, the desired LED and both sensors 116, 122 are turned on. The signal received by the sensors is integrated, then the LED and sensors are turned off. This sequence is repeated for each LED.

These measurements are processed by the controller 120 to make the color determination in block 220. In some embodiments, the controller 120 stores values that correlate sensor values with associated color data, which is used in the color measurement process.

As noted herein, color measurement accuracy can vary if the position of the system 100 is moved away from its nominal height position relative to the test patch 112. Thus, to maintain the color measurement accuracy over varying heights, the color determination is adjusted in block 222 using the color adjustment from block 214.

In some embodiments, a gain factor of the sensor's 116 output signal is adjusted based on color adjustment determined in block 214. As noted above, this can include determining the ratio of the reflected light received from the first LED 110a to the reflected light received from the second LED 110b. This ratio provides an indication of the distance between the light sources 110 and the color patch 112, and can thus further be used to calculate this distance. In other embodiments, for example, the controller stores a color correction matrix including color data adjustments for corresponding to associated color adjustments. The adjusted data can then be transformed to LAB values for a specific illuminant, for example.

As noted above, some embodiments include the calibration sensor 122 in addition to the diffuse sensor 116, which compensates for LED warm-up drift. This further allows the system to acquire the color adjustment information and color measurements quickly because it does not require the LEDs to warm up. In one particular embodiment, 0.3 ms are required for each LED reading. Thus, a complete color adjustment measurement (two sequential readings) takes 0.6 ms. A color measurement (six sequential readings) takes 1.8 ms. If both the color adjustment and color determination are measured at the same time, it takes 2.1 ms (seven sequential readings), since one of the red LEDs 110*a*, 110*b* is used for both the height and color measurement.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A color analysis system, comprising:
   first and second spaced apart light sources configured to emit light of a first color;
   a first sensor configured to provide an output signal in response to reflected light received from the first and second light sources;
   a controller receiving the output signal and configured to determine a color in response to reflected light received by the first sensor from the first light source and not the second light source, and adjust the color determination in response to reflected light received by the first sensor from the first and second light sources.

2. The color analysis system of claim 1, further comprising a second sensor configured to receive light directly from the first and second light sources, and wherein the first sensor is configured receive light reflected from a test patch from the first and second light sources.

3. The color analysis system of claim 1, wherein the first and second light sources are first and second LEDs.

4. The color analysis system of claim 1, further comprising third and fourth spaced apart light sources, wherein the third and fourth light sources emit light of a second color, and wherein the controller is configured to adjust the color determination in response to light received by the first sensor from the third and fourth light sources.

5. The color analysis system of claim 1, wherein the controller is configured to adjust the color determination in response to a ratio of intensity of light received from the first light source to intensity of light received from the second light source.

6. The color analysis system of claim 1, further comprising a plurality of additional light sources, wherein the controller is configured to determine the color in response to light received by the first sensor from the plurality of light sources, and adjust the color determination in response to light received by the first sensor from the first and second light sources.

7. The color analysis system of claim 1, wherein the controller is configured to adjust a gain factor of the output signal in response to light received by the first sensor from the first and second light sources.

8. A color analysis method, comprising:
   receiving reflected light at a sensor from first and second light sources, wherein the first and second light source emit light of a first color;
   determining a ratio of intensity of the reflected light received from the first light source to intensity of the reflected light received from the second light source;
   determining a color in response to the reflected light received from the first light source and not the second light source; and
   adjusting the determined color in response to the determined ratio.

9. The method of claim 8, further comprising:
   a first illumination with the first and second light sources to determine the ratio; and
   a second illumination with the first light source to determine the color.

10. The method of claim 9, wherein the light from the first and second light sources is reflected off of a test patch, the method further comprising determining the distance between the first and second light sources and the test patch in response to the received light.

11. The method of claim 8, further comprising:
    receiving reflected light from third and fourth light sources, wherein the third and fourth light sources emit light of a second color;
    determining a ratio of intensity of the reflected light received from the third light source to the reflected light received from the fourth light source.

12. The method of claim 11, further comprising
    selecting the ratio of the first and second light sources or the ratio of the third and fourth light sources based on a predetermined criterion; and
    adjusting the determined color in response to the selected ratio.

13. The method of claim 8, wherein the reflected light from the first and second light sources is received by a first sensor.

14. The method of claim 13, wherein the light from the first and second light sources is also received by a second sensor to determine intensity of the emitted light.

15. The method of claim 13, further comprising:
    receiving reflected light from a plurality of additional light sources by the first sensor;
    wherein the color is determined further in response to the reflected light received from the plurality of light sources.

16. The method of claim 8, wherein adjusting the determined color includes adjusting a gain factor applied to the output signal.

17. A color analysis method, comprising:
    receiving reflected light at a sensor from first and second light sources, wherein the first and second light source emit light of a first color;

determining a ratio of intensity of the reflected light received from the first light source to intensity of the reflected light received from the second light source;

determining a color in response to the reflected light received from the first light;

adjusting the determined color in response to the determined ratios;

receiving reflected light at the sensor from third and fourth light sources, wherein the third and fourth light sources emit light of a second color; and determining a ratio of intensity of the reflected light received from the third light source to intensity of the reflected light received from the fourth light source.

18. The method of claim 17, further comprising selecting the ratio of the first and second light sources or the ratio of the third and fourth light sources based on a predetermined criterion; and adjusting the determined color in response to the selected ratio.

* * * * *

UNITED STATES PATENT AND TRADEMARK OFFICE
CERTIFICATE OF CORRECTION

PATENT NO. : 8,149,405 B2
APPLICATION NO. : 12/436240
DATED : April 3, 2012
INVENTOR(S) : Jeffrey M. DiCarlo et al.

It is certified that error appears in the above-identified patent and that said Letters Patent is hereby corrected as shown below:

In column 6, line 28, in Claim 10, delete "claim 9," and insert -- claim 8, --, therefor.

In column 6, line 39, in Claim 11, delete "to" and insert -- to intensity of --, therefor.

In column 6, line 66, in Claim 17, delete "source" and insert -- sources --, therefor.

In column 7, line 6, in Claim 17, delete "light;" and insert -- light source; --, therefor.

In column 7, line 8, in Claim 17, delete "ratios;" and insert -- ratio; --, therefor.

Signed and Sealed this
Thirteenth Day of November, 2012

David J. Kappos
*Director of the United States Patent and Trademark Office*